(12) United States Patent
Bhargava et al.

(10) Patent No.: US 10,828,375 B2
(45) Date of Patent: Nov. 10, 2020

(54) DISTRIBUTION OF ENGINEERED-CYSTEINE CAPS

(71) Applicant: SEATTLE GENETICS, INC., Bothell, WA (US)

(72) Inventors: Swapnil Bhargava, Kirkland, WA (US); Cheng-Wei Aaron Chen, Bothell, WA (US); Matthew J. Leith, Issaquah, WA (US)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 16/347,919

(22) PCT Filed: Nov. 6, 2017

(86) PCT No.: PCT/US2017/060182
§ 371 (c)(1),
(2) Date: May 7, 2019

(87) PCT Pub. No.: WO2018/085769
PCT Pub. Date: May 11, 2018

(65) Prior Publication Data
US 2019/0290777 A1  Sep. 26, 2019

Related U.S. Application Data

(60) Provisional application No. 62/418,572, filed on Nov. 7, 2016.

(51) Int. Cl.
*A61K 39/00* (2006.01)
*A61K 47/68* (2017.01)
*A61K 51/10* (2006.01)
*C07K 16/28* (2006.01)
*C07K 16/00* (2006.01)

(52) U.S. Cl.
CPC .......... *A61K 47/6889* (2017.08); *A61K 51/10* (2013.01); *C07K 16/00* (2013.01); *C07K 16/28* (2013.01); *C07K 2317/14* (2013.01); *C07K 2317/52* (2013.01)

(58) Field of Classification Search
CPC .................................................. A61K 47/6889
See application file for complete search history.

(56) References Cited

U.S. PATENT DOCUMENTS

| | | |
|---|---|---|
| 2008/0096252 A1 | 4/2008 | Zamost et al. |
| 2016/0040207 A1 | 2/2016 | Jerums et al. |
| 2016/0130624 A1 | 5/2016 | Laird et al. |

FOREIGN PATENT DOCUMENTS

| | | |
|---|---|---|
| WO | WO2015/085003 A1 | 6/2015 |
| WO | WO2015/157595 A1 | 10/2015 |
| WO | WO2016/103146 A1 | 6/2016 |
| WO | WO2018/085769 A1 | 5/2018 |
| WO | WO2018/146585 A1 | 8/2018 |

OTHER PUBLICATIONS

Chen, et al., "Charge-based analysis of antibodies with engineered cysteines", mAbs, 1:6, 563-571, (2009).
Junutula, et al., "Site-specific conjugation of a cytotoxic drug to an antibody improves the therapeutic index", Nature Biotechnology, vol. 26, No. 8, pp. 925-932.
PCT Application No. PCT/US2017/060182, Search Report and Written Opinion dated Mar. 26, 2018, 13 pages.
PCT Application No. PCT/US2017/060182, International Preliminary Report on Patentability dated May 16, 2019, 9 pages.
Zhong, et al., "Mechanistic understanding of the cysteine capping modifications of antibodies enables selective chemical engineering in live mammalian cells", Journal of Biotechnology, 248:48-58, (2017).
EP Application No. 17866605.3, extended European Search Report and Search Opinion dated Jun. 19, 2020, 8 pages.
Chen, et al., "Charge-based analysis of antibodies with engineered cysteines", mAbs, vol. 1, No. 6, pp. 563-571, (2011).

*Primary Examiner* — Albert M Navarro
(74) *Attorney, Agent, or Firm* — Seattle Genetics, Inc.

(57) ABSTRACT

The present invention provides a method for removing cysteine caps from antibodies and re-capping the antibodies with cysteine molecules. The methods include, inter alia, culturing a host cell comprising a protein molecule having at least one capped engineered cysteine residue, and contacting the cell culture with cystine. Dissolved oxygen levels can be manipulated in the cell culture to further enhance the removal and re-capping process.

23 Claims, 4 Drawing Sheets

DISTRIBUTION OF ENGINEERED-CYSTEINE CAPS

CROSS-REFERENCE TO RELATED APPLICATIONS

This application is a U.S. national stage filing under 35 U.S.C. 371 of International Application No. PCT/US2017/060182, filed Nov. 6, 2017, which claims the benefit of provisional U.S. Appl. Ser. No. 62/418,572, filed Nov. 7, 2016, which is incorporated herein in its entirety for all purposes.

BACKGROUND OF THE INVENTION

Monoclonal antibodies (mAbs) in which selected amino acids have been mutated to cysteine (i.e., engineered cysteine mAbs, or ecmAbs) are particularly suitable for use in conjugates (e.g., antibody drug conjugates, or ADCs) because conjugates that include ecmAbs have favorable properties including homogeneity in drug-to-antibody ratio (DAR), favorable pharmacokinetics, stability, and solubility. The cysteine mutations are placed in locations in the amino acid sequence of the antibody which generally does not form inter- or intra-chain disulfide bonds, and expression machinery inside the cell producing the mutant mAb treats the cysteine residues as unpaired cysteines. Consequently, the engineered cysteines are generally expressed in the form of mixed disulfides with non-encoded cysteine molecules (i.e., the engineered cysteines are "capped" with capping agents, e.g., cysteine (cys-caps), homocysteine (hcy-caps), cysteinyl glycine (cysgly-caps), or glutathione (gsh-caps), to form engineered cysteine caps (EC-caps)).

In any batch of engineered cysteine antibodies, the highly reactive thiol of the engineered cysteine is usually protected by a range of EC-cap species. While ecmAbs do not impact the final mAb or ADC, the heterogeneity in EC-caps on the ecmAbs can appear as different peaks in imaged capillary isoelectric focusing (icIEF) profiles, whereas the icIEF profiles of ecmAbs having the same EC-cap species are consistent. Inconsistent icIEF profiles could result in rejection of Good Manufacturing Practice (GMP) batches, since icIEF is a commonly used antibody release assay for intermediate antibody materials during mAb and ADC production. Heterogeneous EC-cap distributions can be converted to a single EC-cap species (cys-caps) by extending the duration of the cell culture, but this is restrictive and costly, and could affect product quality. The present invention addresses this and other problems.

BRIEF SUMMARY OF THE INVENTION

The invention provides, inter alia, a method for removing a cysteine cap from a protein molecule by culturing a host cell comprising a protein molecule having at least one capped cysteine residue, and contacting the host cell culture with cystine, whereby the cysteine cap is removed from the protein molecule. In an embodiment, the host cell culture is further contacted with dissolved oxygen (DO). In a further embodiment, simultaneously or subsequent to contacting the host cell culture with cystine, the host cell culture is contacted with a first manipulation of DO at a set point of 0%-50% DO, and subsequent to contacting the host cell culture with the first manipulation of DO, the host cell culture is contacted with a second manipulation of DO at a set point of 20%-100% DO. In an embodiment, the host cell culture is contacted with the first manipulation of DO for 0.5-8 hours. In an embodiment, the host cell culture is contacted with the second manipulation of DO for 0.5-8 hours. In an embodiment, the first manipulation of DO is at a set point of 0% DO. In an embodiment, the second manipulation of DO is at a set point of 100% DO.

In an embodiment, the protein described above is an antibody. In a further embodiment, the antibody is combined with a drug-linker compound under conditions sufficient to form an antibody-drug conjugate. In a further embodiment, the antibody has at least two engineered cysteine residues. In an embodiment, the engineered cysteine residues are present in the heavy constant region of the antibody molecule. In another embodiment, the engineered cysteine residues are present in the heavy chain or light chain variable region of the antibody molecule. In an embodiment, the cysteine cap is an engineered cysteine cap (EC-cap).

In an embodiment, the host cell culture is contacted with cystine on day 10 of the host cell culture. In another embodiment, the host cell culture is contacted with cystine daily throughout the host cell culture duration. In another embodiment, the host cell culture is contacted with cystine on the final day of the host cell culture duration. In an embodiment, the cystine is added at a concentration of between 0.1 mM and 5 M. In a further embodiment, the cystine is added at a concentration of 4 mM.

DETAILED DESCRIPTION OF THE INVENTION

I. General

Figure 1:
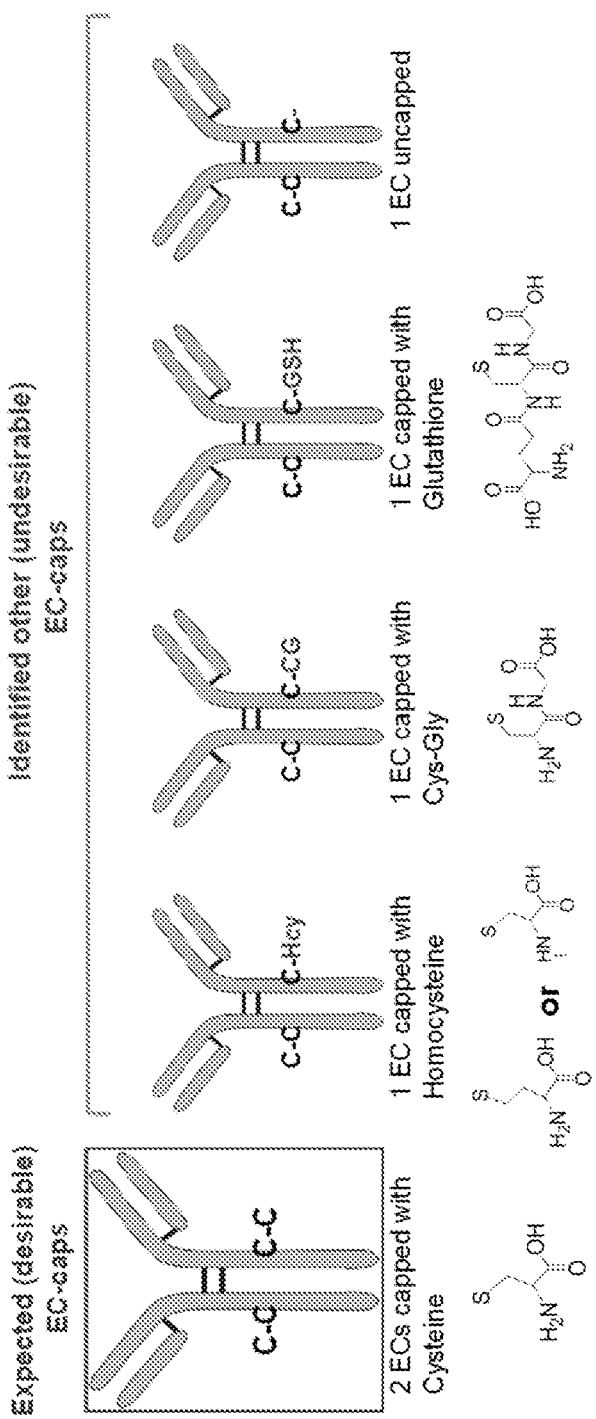
FIG. 1 shows antibodies having a range of engineered-cysteine cap species, including cysteine (-cys, or cys-caps), homocysteine (-hcy, or hcy-caps), cysteinylglycine (-cysgly, or cysgly-caps) and glutathione (-gsh, or gsh-caps).

The present invention provides, inter alia, a method for removing engineered cysteine caps (EC-caps) of different species (e.g., cysteine, homocysteine, cysteinyl glycine, and/or glutathione) from proteins in cell culture, whereby the engineered cysteines of the proteins are then re-capped with a consistent desired cap species (e.g., one of cysteine, homocysteine, cysteinyl glycine, and glutathione). In an embodiment, the method includes contacting a cell culture comprising ecmAbs with a cystine solution, under conditions sufficient to uncap the engineered cysteine residues and re-cap the residues with cys-caps. Adding cystine solution into the cell culture can be preferable to adding cystine solution after the antibody has been harvested, since it addresses the potential heterogeneity of EC-caps in intermediate mAb materials and ensures that EC-cap distributions are controlled at the cell culture process level. In some embodiments, the dissolved oxygen (DO) levels are manipulated in the cell culture to further enhance the uncapping/re-capping processes. The methods of the invention provide, inter alia, consistency across icIEF, and other charge-based assays, profiles and a simplification of current manufacturing practice for preparation of mAbs and ADCs.

II. Definitions

As used herein, the terms "antibody" broadly refers to intact monoclonal antibodies, polyclonal antibodies, monospecific antibodies, multispecific antibodies (e.g., bispecific antibodies), and antibody fragments that exhibit the desired biological activity (i.e., specific binding to a target antigen) and that have at least one native inter-chain disulfide bond. Exemplary fragments include, for example, Fabs, minibodies and the like. An intact antibody is typically composed of four polypeptide chains (two heavy chains and two light chains), each polypeptide having primarily two regions: a variable region and a constant region. The variable region specifically binds to and interacts with a target antigen. The variable region includes complementarity determining regions (CDRs) that recognize and bind to a specific binding site on a particular antigen. The constant region may be recognized by and interact with the immune system (see, e.g., Janeway et al., 2001, *Immuno. Biology*, 5th Ed., Garland Publishing, New York). The four polypeptide chains are covalently linked to each other via inter-chain disulfide bonds. An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some embodiments, the antibody is of human or murine origin. A monoclonal antibody can be, for example, human, humanized, or chimeric. Depending on the context, the term "antibody" can refer to a singular antibody molecule or a collection of antibody molecules, such as in an antibody solution.

As used herein, the term "inter-chain disulfide bond" refers to a covalent bond between two cysteine residues on adjacent polypeptide chains in an antibody. The disulfide bond has the formula $R^1$—S—S—$R^2$, wherein the sulfur atoms are present in the cysteine sidechains and $R^1$ and $R^2$ represent the remainder of the cysteine residues and the polypeptide chains in which they reside. An inter-chain disulfide bond is generally present between a heavy chain and a light chain in an antibody, or between the two heavy chains.

As used herein, the term "engineered cysteine residue" refers to a cysteine residue that is introduced into the peptide sequence of a protein (e.g., antibody). A monoclonal antibody having an engineered cysteine residue can be referred to as an "ecmAb." The engineered cysteine residue is generally not present in the native (i.e., naturally-occurring) peptide sequence of the protein. The engineered cysteine residue can take the place of the amino acid that naturally occurs at a given position in the peptide sequence, and can be introduced into the peptide sequence via recombinant techniques such as site-directed mutagenesis. The engineered cysteine residue can be capped or uncapped.

As used herein, the term "uncapped cysteine residue" refers to a cysteine residue wherein the α-sidechain contains a free thiol moiety having the formula $R^1$—SH. $R^1$ represents the non-thiol portion of the cysteine residue. The uncapped cysteine residue can be an uncapped engineered cysteine residue.

As used herein, the term "capped cysteine residue" refers to a cysteine residue wherein the α-sidechain contains a disulfide moiety having the formula $R^1$—S—S—$R^3$. $R^1$ represents the non-thiol portion of the cysteine residue, and $R^3$ represents the non-thiol portion of a capping moiety having a molecular weight less than or equal to about 500 Da. The cap can be, for example, cysteine, homocysteine, cysteinyl glycine, or glutathione (with $R^3$ representing the non-thiol portion of free cysteine, cysteinyl glycine, or the non-thiol portion of glutathione, respectively) or any other available monothiol. The capped cysteine residue can be a capped engineered cysteine residue.

As used herein, "removing" a substance, such as an EC-cap (or cap byproduct), from a protein refers to removing any portion of the substance, including the entirety of the substance, from the protein.

As used herein, "re-capping" a substance, such as an EC-cap (or cap byproduct), on a protein refers to reformation of any portion of the substance, including the entirety of the substance, onto the protein.

As used herein, the terms "antibody-drug conjugate" and "ADC" refer to an antibody conjugated to a therapeutic agent, (i.e., a drug) optionally via a linker.

As used herein, the term "drug-linker compound" or "drug-linker" refers to a molecule having a drug moiety and a linker attached thereto, wherein the linker contains a reactive moiety suitable for attachment to an amino acid residue (such as a cysteine residue) in an antibody.

III. Description of the Embodiments

The present invention provides, inter alia, a method for removing engineered cysteine caps (EC-caps) from ecmAbs and reforming a desired cap species on the ecmAbs. In an embodiment, the method includes contacting a cell culture comprising ecmAbs with a cystine solution, under conditions sufficient to uncap engineered cysteine residues and re-cap the residues with cysteine.

Cell Culture Conditions

In some embodiments, ecmAbs are produced and harvested from a host cell culture. FIG. 1 shows various examples of EC-caps on the engineered cysteine residues of antibodies. In any cell culture, antibodies with engineered cysteine residues may be capped with any or all of the EC-cap species shown in FIG. 1. Methods of the invention can be used to create a consistency among the EC-caps of ecmAbs in a cell culture, for example to remove the EC-caps and re-cap the engineered cysteine residues with cys-caps. In some such aspects, the engineered cysteine residue will be at position 239 of the heavy chain (numbering according to the EU index described by Kabat et al., "Sequences of proteins of immunological interest, 5th ed., Pub. No. 91-3242, U.S. Dept. Health & Human Services, NIH, Bethesda, M. D., 1991) of the antibody. The cell culture can comprise any mammalian cell line, including CHO cells. The media used for cell culture can be any media, including RPMI. In some embodiments, the media already contains cystine at a low concentration. However, the low amount of cystine in media is generally not sufficient to remove and re-cap EC-caps from ecmAbs.

The cell culture can include any suitable amount of the ecmAbs. Typically, the concentration of protein (whether antibody or non-antibody protein) in the cell culture ranges from about 0.01 mg/mL to about 150 mg/mL or higher, more typically from about 1 mg/ml to about 50 mg/ml. The cell culture can contain, for example, about 0.01, 0.05, 0.1, 0.25, 0.5, 1.0, 2.0, 3.0, 4.0, 5.0, 6.0, 7.0, 8.0, 9.0, 10.0, 12.5, 15, 17.5, 20, 22.5, 25, 30, 35, 40, 45, 50, 55, 60, 65, 70, 75, 80, 85, 90, 95, 100, 110, 120, 130, 140, or about 150 mg of protein (whether antibody or non-antibody protein) per mL of the cell culture. One of skill in the art will be able to convert a mass-based concentration (e.g., mg/mL) to a molar concentration (i.e., moles/L).

To remove the EC-caps from ecmAbs and re-cap with cysteine, cystine solution is added to the cell culture. The cystine solution can be any kind of solution, such as an acidic or basic solution, or the cystine can be present in cell culture media (e.g., feed media or basal media). The cystine solution can be added to the cell culture by any method, including direct injection. In other embodiments, a different solution is added to the cell culture, such as homocysteine disulfide, or any symmetrical disulfide. In some embodiments, both the monomer and dimer of the desired EC-cap are added to facilitate an EC-cap exchange, e.g., cysteine and cystine are added to the cell culture. In an embodiment, the EC-cap species used to re-cap the engineered cysteine residues is dependent on the symmetrical disulfide added to the cell culture. For example, if cystine is added, the ecmAbs will be re-capped with cysteine; if homocysteine disulfide is added, the ecmAbs will be re-capped with homocysteine.

Any suitable amount of cystine solution (or other symmetrical disulfide) can be used in the methods of the invention. In general, the concentration of the symmetrical disulfide added to the cell culture is high enough to uncap and re-cap the engineered cysteine residues of the antibodies. In some embodiments, cystine is added at a concentration between 0.1 mM and 5 M. In further embodiments, cystine is added at a concentration between 0.1 mM and 1 M, 0.1 mM and 100 mM, 1 mM and 100 mM, 1 mM and 10 mM, or 1 mM and 5 mM. In further embodiments, cystine is added at a concentration of 0.1, 1, 2, 3, 4, 5, 6, 7, 8, 9, 10, 20, 30, 40, 50, 60, 70, 80, 90, 100, 200, 300, 400, 500, 600, 700, 800, or 900 mM, or 1, 2, 3, 4, or 5 M. In some embodiments, the concentration may be increased or decreased. In some embodiments, the concentration of cystine will be maintained at a concentration greater than the concentration of total antibody. The concentration of cystine in the cell culture will, in some aspects, be anywhere from about 5 times to about 10,000 times, 5 times to about 5,000 times, 5 times to about 1,000 times, 5 times to about 500 times, 5 times to about 100 times, 5 times to about 20 times, 5 times to about 15 times, or 5 times to about 10 times higher than the concentration of total antibody in the cell culture. For example, in some embodiments, the concentration ratio of cystine to total antibody in the cell culture will be about 5:1, 6:1, 7:1, 8:1, 9:1, 10:1, 11:1, 12:1, 13:1, 14:1, 15:1, 16:1, 17:1, 18:1, 19:1, 20:1, 25:1, 50:1, 100:1 or more.

In some embodiments, cystine (or other symmetrical disulfide) is added every day for the duration of the cell culture. In other embodiments, cystine is only added on certain days, for example day 10 of the cell culture. In some embodiments, cystine is added on any or all of the following days of the cell culture: day 1, day 2, day 3, day 4, day 5, day 6, day 7, day 8, day 9, day 10, day 11, day 12, day 13, day 14, day 15, or any day higher than day 15, such as day 20, day 25, day 30, day 35, day 60, day 90, or any day higher than day 90. In an embodiment, cystine is added on the final day of the cell culture duration. Cystine can be added once, twice, three times, or four or more times throughout the duration of the cell culture. In an embodiment, cystine is added to the cell culture on the day the antibody is harvested from the cell culture.

Any suitable amount of dissolved oxygen can be used in the methods of invention. In some embodiments, the DO set point is manipulated in the cell culture after the addition of cystine. In other embodiments, the DO set point is manipulated before the addition of cystine, or simultaneously with the addition of cystine. In an embodiment, the DO is reduced to anywhere between 0% and 99% (where 100% DO is 100% of air saturation, or ~21% of oxygen) before, during, or after the addition of cystine, in order to create a reduced environment. For example, the DO can be reduced to a set point between 0%-90%, 0%-50%, 0%-30%, 0%-20%, 0%-10%, 10%-50%, 10%-40%, 10%-30%, 10%-20%, or a set point of 0%, 10%, 20%, 30%, 40%, 50%, 60%, 70%, 80%, or 90%. The DO can be reduced for any duration of time after the addition of cystine, including 0.5-10 hours, 0.5-4 hours, 0.5-2 hours, 0.5-8 hours, 0.5-10 hours, 1-10 hours, 1-4 hours, 1-2 hours, 5 minutes, 30 minutes, 1 hour, 2 hours, 3 hours, 4 hours, 5 hours, 6 hours, 7 hours, 8 hours, 9 hours, or 10 or more hours. After the DO is reduced, the DO is then increased to anywhere between 1% and 500% for any duration of time. For example, the DO can be increased to a set point between 10%-500%, 20%-500%, 30%-500%, 40%-500%, 50%-500%, 60%-500%, 70%-500%, 80%-500%, 90%-500%, 10%-100%, 20%-100%, 30%-100%, 40%-100%, 50%-100%, 60%-100%, 70%-100%, 80%-100%, 90%-100%, or a set point of 10%, 20%, 30%, 40%, 50%, 60%, 70%, 80%, 90%, or 100%. The DO can be increased for any duration of time, including 0.5-10 hours, 0.5-4 hours, 0.5-2 hours, 1-10 hours, 1-4 hours, 1-2 hours, 5 minutes, 30 minutes, 1 hour, 2 hours, 3 hours, 4 hours, 5 hours, 6 hours, 7 hours, 8 hours, 9 hours, or 10 or more hours. The DO can be added by any method, including sparging with air and oxygen and/or overlay.

Antibody Conjugates

Uncapped engineered cysteine residues on an antibody serve as useful handles for installation of a variety of functional groups, including imaging agents (such as chromophores and fluorophores), diagnostic agents (such as MRI contrast reagents and radioisotopes), stability agents (such as polyetheylene glycol polymers) and therapeutic agents. During the conjugation process, the different EC-caps of the ecmAbs will be removed, resulting in uncapped cysteine residues. Antibodies having uncapped cysteine residues can be conjugated to functional agents to form antibody-functional agent-conjugates. The functional agent (e.g., drug, detection agent, stability agent) is conjugated (covalent attachment) to the antibody at the site of an engineered cysteine residue. A functional agent can be attached indirectly via a linker or directly via a thiol-reactive group on the functional agent.

Antibodies having uncapped cysteine residues can be conjugated to drugs to form antibody drug conjugates (ADCs). Typically, the ADC contains a linker between the drug and the antibody. The linker can be a cleavable or a non-cleavable linker. A cleavable linker is typically susceptible to cleavage under intracellular conditions such that cleavage of the linker releases the drug from the antibody at the target site. Suitable cleavable linkers include, for example, enzyme cleavable linkers including peptidyl containing linkers cleavable by an intracellular protease, such as lysosomal protease or an endosomal protease or sugar linkers for example, glucuronide containing linkers cleavable by a glucuronidase. Peptidyl linkers can include, for example, a dipeptide, such as valine-citrulline (val-cit) phenylalanine-lysine (phe-lys) or valine-alanine (val-ala). Other suitable cleavable linkers include, for example, pH-sensitive linkers (e.g., linkers hydrolyzable at a pH of less than 5.5, such as a hydrazone linker) and linkers cleavable under reducing conditions (e.g., disulfide linkers). Non-cleavable linkers typically release drugs by proteolytic degradation of the antibody.

Prior to attachment to the antibody, the linker will have a group reactive with the uncapped engineered cysteine residues and attachment will be via the reactive group. Thiol-specific reactive groups are preferred and include, for example, maleimides; haloacetamides (e.g., iodo, bromo or chloro); haloesters (e.g., iodo, bromo or chloro); halomethyl ketones (e.g., iodo, bromo or chloro); benzylic halides (e.g., iodide, bromide or chloride); vinyl sulfones; (pyridyl)disulfides; disulfide dioxide derivatives; mercury derivatives such as 3,6-bis-(mercurimethyl)dioxane with counter ions of acetate, chloride or nitrate; and polymethylene bismethane thiosulfonates. The linker can include, for example, a maleimide that attaches to the antibody via a thio-succinimide linkage.

The drug can be any cytotoxic, cytostatic or immunosuppressive drug. In embodiments wherein a linker links the antibody and the drug, the drug has a functional group that can form a bond with the linker. For example, the drug can have an amine, a carboxylic acid, a thiol, a hydroxyl group, or a ketone that can form a bond with the linker. In aspects wherein the drug is directly attached to the linker, the drug will, prior to attachment to the antibody, have a group reactive with uncapped engineered cysteines.

Useful classes of drugs include, for example, antitubulin agents, DNA minor groove binders, DNA replication inhibitors, alkylating agents, antibiotics, antifolates, antimetabolites, chemotherapy sensitizers, topoisomerase inhibitors, vinca alkaloids, or the like. Particularly examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids (e.g., DM1 and DM4), taxanes, benzodiazepines or benzodiazepine containing drugs (e.g., pyrrolo[1,4]-benzodiazepines (PBDs), indolinobenzodiazepines, and oxazolidinobenzodiazepines) and vinca alkaloids. Select benzodiazepine containing drugs are described in WO 2010/091150, WO 2012/112708, WO 2007/085930, and WO 2011/023883.

In some typical embodiments, suitable cytotoxic agents include, for example, DNA minor groove binders (e.g., enediynes and lexitropsins, a CBI compound; see also U.S. Pat. No. 6,130,237), duocarmycins (see U.S. Publication No. 20060024317), taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

The drug can be an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, auristatins, and eleutherobin.

The drug can be a maytansine or a maytansinoid, another group of anti-tubulin agents. (ImmunoGen, Inc.; see also Chari et al., 1992, Cancer Res. 52:127-131 and U.S. Pat. No. 8,163,888).

The drug can be an auristatin. Auristatins include, but are not limited to, AE, AFP, AEB, AEVB, MMAF, and MMAE. The synthesis and structure of auristatins are described in U.S. Patent Application Publication Nos. 2003-0083263 and 2009-0111756; International Patent Publication No. WO 04/010957; International Patent Publication No. WO 02/088172; U.S. Pat. Nos. 6,884,869; 7,659,241; 7,498,298; 8,343,928; and 8,609,105; each of which is incorporated by reference in its entirety and for all purposes.

In some embodiments, the drug moiety is selected from the group consisting of an anti-tubulin agent, a DNA binding agent, and a DNA alkylating agent. In some embodiments, the drug is selected from the group consisting of an auristatin, a pyrrolobenzodiazepine, a duocarmycin, a maytansinoid, a taxane, a calicheamicin, and an anthracycline.

A drug-linker can be used to form an ADC in a single step. In other embodiments, a bifunctional linker compound can be used to form an ADC in a two-step or multi-step process.

Generally, a functional group on the linker is selected for specific reaction with a suitable reactive group in the drug moiety. As a non-limiting example, an azide-based moiety can be used for specific reaction with a reactive alkyne group in the drug moiety. The drug is covalently bound to the linker via 1,3-dipolar cycloaddition of the azide and alkyne. Other useful functional groups include, for example, ketones and aldehydes (suitable for reaction with hydrazides and alkoxyamines); phosphines (suitable for reaction with azides); isocyanates and isothiocyanates (suitable for reaction with amines and alcohols); and activated esters such as N-hydroxysuccinimidyl esters (suitable for reaction with amines and alcohols). These and other linking strategies, as described, for example, in *Bioconjugate Techniques*, 2$^{nd}$ Ed. (Elsevier), are well known to those of skill in the art. One of skill in the art will appreciate that when a complementary pair of reactive functional groups is chosen for selective reaction of the drug moiety to the linker, each member of the pair can be employed on either the linker or the drug.

Some embodiments of the invention provide methods for combining ecmAbs with a drug-linker compound under conditions sufficient to form an antibody-drug conjugate (ADC). In some embodiments, the methods include combining ecmAbs with a bifunctional linker compound, under conditions sufficient to form an antibody-linker conjugate. In such embodiments, the methods of the invention can further include combining the antibody-linker conjugate with a drug moiety under conditions sufficient to covalently link the drug moiety to the antibody via the linker.

In some embodiments, the ADC is of the following formula:

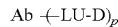

wherein
  Ab is an antibody,
  LU is a linker,
  D is a drug;
  and the subscript p is a value from 1 to 8.

Drug Loading

The average number of drug-linker molecules per antibody (or average drug load) is an important characteristic of an ADC composition, as it is a primary determinant of the amount of drug that can be delivered to a target cell. The average drug load includes drugs conjugated to engineered cysteine residues, as well as drugs conjugated to sites other than the intended engineered cysteine residues and the amount of unconjugated antibodies in the composition. When an average drug loading of about two drugs per antibody is targeted, antibodies having two engineered cysteine residues (e.g., one site on each heavy chain or one site on each light chain) can be used to prepare the ADC composition. When an average drug loading of about four drugs per antibody is targeted, antibodies having four engineered cysteine residues (e.g., two sites on each heavy chain, or two sites on each light chain, or one site on the heavy chain and one site on the light chain) can be used to prepare the ADC composition. One of skill in the art will appreciate that other levels of drug loading can be therapeutically useful depending on the particular antibody or the particular drug (including, for example, drug loading levels less than 2 as well as drug loading levels greater than 4). Sites for drug conjugation can be introduced in an antibody by placing engineered cysteines at more than one site or more than two sites in the heavy chain, or by placing an engineered cysteine in the light chain, or both.

Typically, ADC compositions prepared with antibodies having two engineered cysteine residues have an average drug-loading of from about 1.5 to 2.5 drugs per antibody. The average number of drug moieties per antibody can be, for example, about 1.5, 1.6, 1.7, 1.8, 1.9, 2.0, 2.1, 2.2, 2.3, 2.4, or 2.5. In some embodiments, the average drug-loading for ADC compositions prepared with antibodies having two engineered cysteine residues is from about 1.5 to about 2.2 drug moieties per antibody, or from about 1.8 to about 2 drug moieties per antibody. Typically, ADC compositions prepared with antibodies having four engineered cysteine residues have an average drug-loading of from about 3.4 to 4.5 drug moieties per antibody. The average number of drug moieties per antibody can be, for example, about 3.3, 3.4, 3.5, 3.6, 3.7, 3.8, 3.9, or 4.0. In some embodiments, the average drug-loading for ADC compositions prepared with antibodies having four engineered cysteine residues is from about 3.6 to about 4.2 drug moieties per antibody, or from about 3.8 to about 4 drug moieties per antibody.

Various analytical methods can be used to determine the yields and isomeric mixtures of the conjugates. Following conjugation of the drug to the antibody, the conjugated drug-antibody species can be separated. In some embodiments, the conjugated antibody species can be separated based on the characteristics of the antibody, the drug and/or the conjugate. Other techniques useful for analysis of ADC compositions include, but are not limited to, reversed-phase chromatography, capillary electrophoresis, and mass spectrometry. ADC compositions can be analyzed, for example, by LC/MS coupled with proteolytic digestion to determine the location of a drug moiety in an ADC.

Antibodies

A number of suitable antibodies can be used in the methods of the invention. Antibodies used in the methods of the invention are useful for a number of applications, including in vitro or in vivo diagnosis, in vivo imaging, and therapy for diseases and conditions associated with distinctive antigens. Five human antibody classes (IgG, IgA, IgM, IgD and IgE), as well as various subclasses (e.g., IgG1, IgG2, IgG3, IgG4, IgA1 and IgA2) within these classes, are recognized on the basis of structural differences, such as the number of immunoglobulin units in a single antibody molecule, the disulfide bridge structure of the individual units, and differences in chain length and sequence. The class and subclass of an antibody is referred to as the antibody's isotype.

The antibody can be an intact antibody or an antigen-binding antibody fragment, provided that the antibody fragment contains at least one unpaired cysteine (cysteines that do not generally form inter-chain or intra-chain bonds within the protein), engineered or native, that is capped with thiols during expression or production.

Typically, the antibodies are human, rodent (e.g., mouse and rat), donkey, sheep, rabbit, goat, guinea pig, camelid, horse, or chicken. The antibody can be, for example, a murine, a chimeric, humanized, or fully human antibody produced by techniques well-known to one of skill in the art. Recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as those having a variable region derived from a murine monoclonal and human immunoglobulin constant regions. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art. As used herein, "human" antibodies include antibodies having the amino acid sequence of a human immunoglobulin and include antibodies isolated from human immunoglobulin libraries, from human B cells, or from animals transgenic for one or more human immunoglobulin, as described for example in U.S. Pat. Nos. 5,939,598 and 6,111,166.

The antibodies may be monospecific, bispecific, trispecific, or of greater multispecificity.

In certain instances, the constant domains have effector function. The term antibody effector function, as used herein refers to a function contributed by an Fc domain(s) of an Ig. Such function can be effected by, for example, binding of an Fc effector domain(s) to an Fc receptor on an immune cell with phagocytic or lytic activity or by binding of an Fc effector domain(s) to components of the complement system. The effector function can be, for example, "antibody-dependent cellular cytotoxicity" or ADCC, "antibody-dependent cellular phagocytosis" or ADCP, "complement-dependent cytotoxicity" or CDC. In certain instances, the constant domain lack one or more effector functions. Conjugation of a drug-linker compound to an engineered cysteine residue located in an effector function binding domain can modulate the effector function.

The antibodies may be directed against any antigen of interest, such as of medical and/or therapeutic interest. For example, the antigen can be one associated with pathogens (such as but not limited to viruses, bacteria, fungi, and protozoa), parasites, tumor cells, or particular medical conditions. In the case of a tumor-associated antigen (TAA), the cancer may be of the immune system, lung, colon, rectum, breast, ovary, prostate gland, head, neck, bone, or any other anatomical location. Antigens of interest include, but are not limited to, CD30, CD40, Lewis Y, CD70, CD2, CD20, CD22, CD33, CD38, CD40, CD52, HER2, EGFR, VEGF, CEA, HLA-DR, HLA-Dr10, CA125, CA15-3, CA19-9, L6, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, gp100, MART1, IL-2 receptor, human chorionic gonadotropin, mucin, P21, MPG, and Neu oncogene product.

Some specific useful antibodies include, but are not limited to, antibodies against the CD33 antigen (e.g., a humanized 2H12 antibody as described in International Application Number WO 2013/173496), antibodies against the CD70 antigen, (e.g., a humanized 1F6 antibody as described in International Application Number WO2006/113909), antibodies against the CD30 antigen (e.g., a humanized AC10 antibody as described in International Application Number WO2008/025020), antibodies against the CD19 antigen (e.g., a humanized BU12 antibody as described in International Application Number WO 2009/052431), antibodies against LIV-1, CD123, NTBA, or alpha V Beta 6. Many other internalizing antibodies that bind to tumor specific antigens can be used, and have been reviewed (see, e.g., Franke et al. (2000), Cancer Biother Radiopharm. 15:459-76; Murray (2000), Semin Oncol. 27:64-70; Breitling et al., Recombinant Antibodies, John Wiley, and Sons, New York, 1998). The disclosures of these references and International Applications are incorporated by reference herein and for all purposes.

In some embodiments, the invention provides methods for preparing an antibody that comprises at least three inter-chain disulfide bonds. In some embodiments, the antibody comprises at least four inter-chain disulfide bonds. In some embodiments, the antibody comprises 1, 2, 3, 4, or 5 inter-chain disulfide bonds. In some embodiments, the engineered cysteine residue is present in the heavy constant region or the light constant region of the antibody.

Engineered Cysteine Sites

The site of the engineered cysteine can have an impact on the properties of a resulting ADC. For instance, engineered cysteines entirely buried in the structure of the protein can be difficult to conjugate because of poor access to the solvent, while engineered cysteines on the exterior surface of the antibody may result in ADCs that have impaired stability because of prolonged exposure to materials in plasma. Also, ADCs prepared from ecmAbs with highly exposed surface engineered cysteines may be sensitive to the hydrophobicity of the drug, while engineered cysteines in more protected locations may be less sensitive to the properties of the drug, because access to other materials in solution is restricted. The location of an engineered cysteine residue can also be used to modulate effector function as desired for a particular ADC. For example, conjugation of a drug-linker to an engineered cysteine residue in an effector function binding domain can be used to block binding to effector function-mediating receptors.

In some embodiments, the engineered cysteine is located in the heavy chain constant region, the heavy chain variable region, the light chain variable region, the light chain constant region, or combinations thereof. Preferred engineered cysteine residues are residues that are located at sites that are conjugatable and result in stable linkages. By conjugatable it is meant that the engineered cysteine residue is capable of being conjugated to a functional agent (e.g., imaging agents, diagnostic agents, stability agents or therapeutic agents) without first denaturing the antibody. Methods for selecting a site for introducing a cysteine residue that can be subsequently conjugated to a functional agent are known in the art (e.g., see, for example, Junutula et al., 2008, Nature Biotechnology, 26(8), 925-932). In some embodiments, an antibody has from 1 to 8 or from 2 to 8 or from 2 to 4 engineered cysteine residues.

In some aspects, the engineered cysteine residue is one that has a fractional solvent accessibility of 10% or above, 20% or above, 30% or above, 40% or above, or 50% or above. In some aspects, the cysteine residue is one that has a fractional solvent accessibility of from about 10% to about 95%, from about 10% to about 85%, from about 10% to about 75%, from about 10% to about 60%, from about 20% to about 95%, from about 20% to about 85%, from about 20% to about 75%, from about 20% to about 60%, or from about 40% to about 95%, from about 40% to about 85%, from about 40% to about 75%, from about 40% to about 60%. Methods for determining the fractional solvent accessibility of a residue at a particular site are known in the art and can be determined, for example, using the online server getarea that uses the methodology described in Fraczkiewicz and Braun, 1998, J. Comp. Chem., 19, 319-333 (see http://curie.utmb.edu/getarea.html). Exemplary residues include those at sites 15, 114, 121, 127, 168, 205, on the light chain (numbering according to Kabat) or sites 112, 114, or 116 on the heavy chain (numbering according to Kabat numbering). Exemplary residues include those in the Fc region of an IgG1 antibody such as those at sites 239, 326, 327, or 269 in the Fc region (numbering according to the EU index). The fraction solvent accessibility of residues at site 239, 326, and 327 is about 50%, about 94%, and about 23%, respectively.

Non-Antibody Proteins

It will be appreciated by those skilled in the art that although the process described herein is exemplified with respect to antibodies, it may be successfully employed for any protein with unpaired cysteines (cysteines that do not generally form inter-chain or intra-chain bonds within the protein), engineered or native, that are capped with thiols during expression or production. The process described herein can also be successfully employed for any protein containing a free thiol as a part of the protein. Proteins for which this process is particularly helpful are proteins that, in addition to comprising unpaired cysteines, contain native cysteines that form inter-chain disulfide bonds, particularly bonds that can be cleaved without immediately resulting in unfolding of the protein. When referring to a non-antibody protein, the term inter-chain disulfide bond refers to a covalent bond between two cysteine residues on adjacent polypeptide chains. Candidate non-antibody proteins include those which contain solvent exposed disulfide bonds whose stability in native folded conformation is comparable to those of the capped thiols. An engineered cysteine protein, as used herein, is one in which selected amino acids in the protein have been mutated to cysteine. Exemplary proteins also include Fc-fusion proteins, e.g., protein containing a Fc region of an antibody covalently linked to a protein that provides specificity for a desired target.

IV. Examples

Example 1: Cell Culture Preparation

Industrial-relevant Chinese hamster ovary (CHO) cell lines were used in this study. The cell lines were derived from a dihydrofolate minus (dhfr-) CHO host (Urlaub G, Chasin L A, Isolation of Chinese hamster cell mutants deficient in dihydrofolate reductase activity. *Proc Natl Acad Sci USA* 77:4216-4220, 1980), and were genetically engineered to secrete recombinant mAbs with an engineered cysteine residue inserted in each of the Fc regions (i.e. S239C). Cells were cultured and maintained in shake flasks using industry-standard chemically-defined basal medium. The shake flask culture conditions were 37° C., 5% $CO_2$ and 125 RPM with 19 mm throw. Cell culture volume was scaled-up 3 to 4 days before starting the production stage in 3 L bioreactors.

A fed-batch cell culture process was used for the bioreactor experiments. The bioreactors (Applikon, Inc.) were equipped with calibrated DO (dissolved oxygen), pH and temperature probes. Temperature control was achieved via a heating blanket. DO was controlled on-line through sparging with air and oxygen, and pH was controlled through additions of $CO_2$ or liquid base. The industrial-standard basal and feed media were used to culture the cells. The process conditions were pH 7.00, 30% DO and 200 RPM with one pitched-blade impeller. The initial temperature set-point was 37° C. and shifted to 33° C. on culture day 4. The initial working volume was 1.2 L, and variable feed volumes were added to the culture from culture day 1 to 9. The glucose concentration was maintained throughout the culture.

Example 2: Uncapping and Recapping Engineered Cysteine Residues on Day 10 of Cell Culture 50 mL of 100 mM cystine solution was added to the cell culture on day 10 to have a final added concentration of 4 mM. The cell culture was allowed to incubate in this condition for 2 hours. 2 hours after cystine addition, the DO was reduced to 0% for 2 hours, and the DO was then increased to 100% for another 2 hours. Samples were taken before and after each manipulation to assess the impact on the EC-cap distributions.

Figure 2:
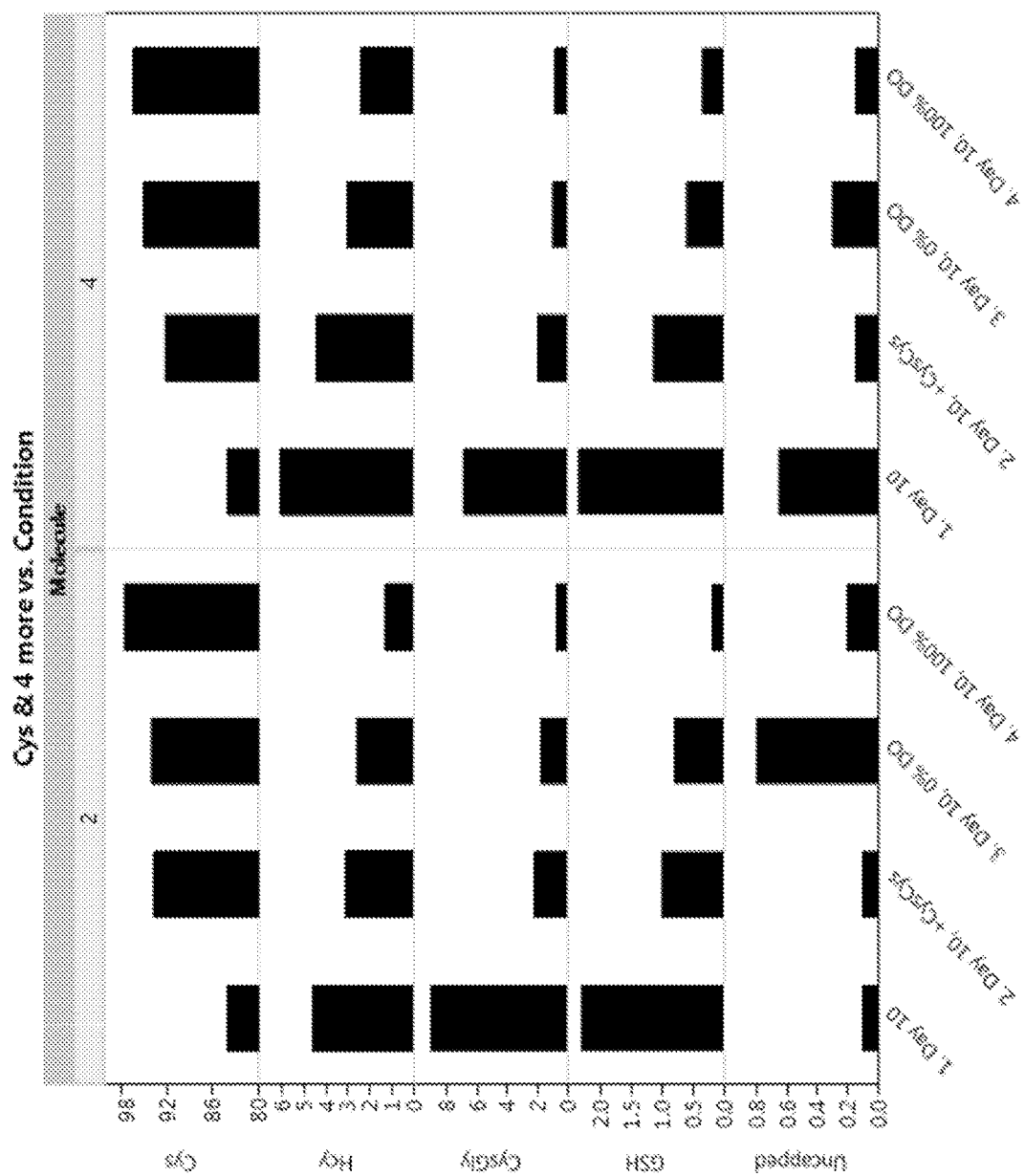
FIG. 2 shows EC-cap distributions after cystine addition and dissolved oxygen manipulations for two molecules, according to an embodiment. Day 10 represents day 10 of the cell culture, +CysCys represents cystine addition, and 0% or 100% DO represents the dissolved oxygen set points.
Figure 3:
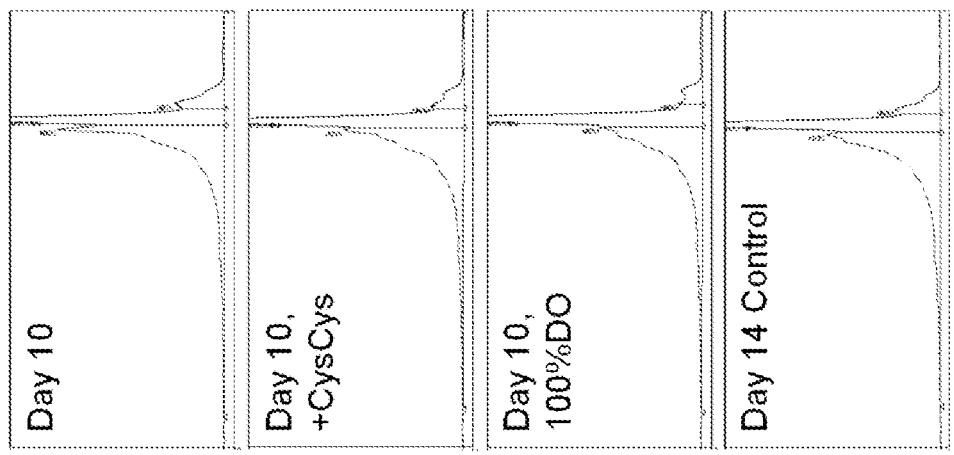
FIG. 3 shows icIEF profiles of ecmAbs in cell culture under different conditions, according to an embodiment.

As shown in FIG. 2, the -cys ecmAbs (ecmAbs re-capped with cys-caps) increased from approximately 84% to 93% after the cystine addition step, and further increased to 97% after the 100% DO manipulation. Typically, percent -cys ecmAbs is indicative of the consistency in the icIEF profile. Studies performed on the model molecules suggest that an increase in -cys ecmAbs correspond to an increased consistency of the icIEF profile. FIG. 3 shows an example of an icIEF profile at day 10 without added cystine or DO manipulation. This profile is inconsistent with the positive control at day 14 (when the cell culture is carried to day 14, icIEF profiles are generally consistent). However, the icIEF profiles at day 10 plus cystine and day 10 plus cystine plus 0% and 100% DO are consistent with this positive control. This method proved to be an effective way to control the heterogeneous EC-cap distributions without compromising the process and product.

Figure 4:
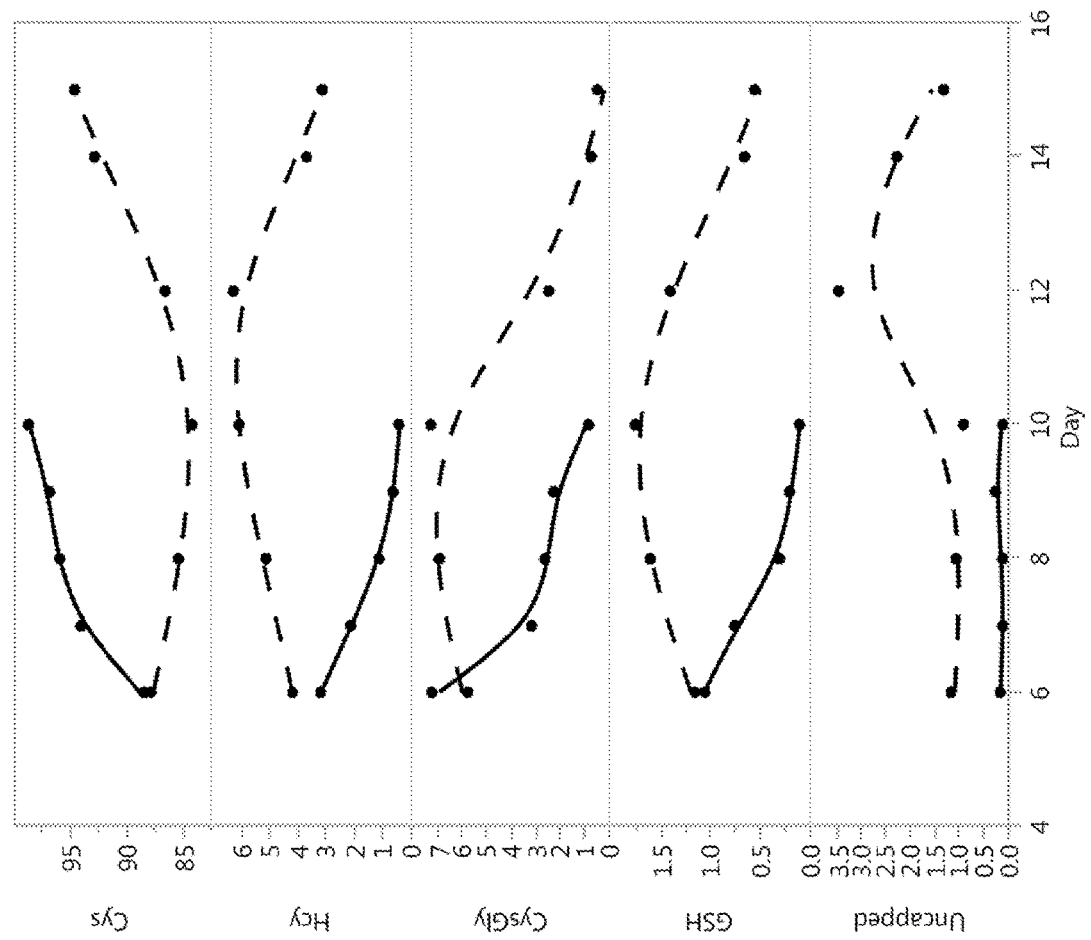
FIG. 4 shows EC-cap distributions over time of a control (dashed line) and with daily cystine addition starting on day 6 (solid line), according to an embodiment.

Example 3: Uncapping and Recapping Engineered Cysteine Residues Throughout Cell Culture Duration In this example, 25 mL of 100 mM cystine solution was added to the culture every day starting on culture day 6. Samples were taken from culture day 6 to day 10 to assess the impact of daily cystine addition on the EC-cap distributions. The impact of cystine addition on culture day 6 was assessed on culture day 7. As illustrated in FIG. 4, the -cys ecmAbs (cysteine-capped re-capped ecmAbs) were above 90% for the daily cystine addition condition from culture day 7 to day 10. The -cys ecmAbs were above 90% for the control condition only after culture day 14.

On culture day 10, the -cys ecmAbs were about 85% and 98% for the control and daily cystine addition conditions, respectively. This method provided an effective way to control the heterogeneous EC-cap distributions on any given culture day without compromising the process and product.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for removing a cysteine cap from a protein molecule, the method comprising:
    culturing a host cell comprising a protein molecule having at least one capped cysteine residue; and
    contacting the host cell culture with cystine;
    whereby the cysteine cap is removed from the protein molecule.

2. The method of claim 1, further comprising contacting the host cell culture with dissolved oxygen (DO).

3. The method of claim 1, further comprising:
    simultaneously or subsequent to contacting the host cell culture with cystine, contacting the host cell culture with a first manipulation of DO at a set point of 0%-50% DO;
    subsequent to contacting the host cell culture with the first manipulation of DO, contacting the host cell culture with a second manipulation of DO at a set point of 20%-100% DO.

4. The method of claim 3, wherein the contacting the host cell culture with the first manipulation occurs for a duration of 0.5-8 hours.

5. The method of claim 4, wherein the contacting the host cell culture with the first manipulation occurs for a duration of 2 hours.

6. The method of claim 3, wherein the contacting the host cell culture with the second manipulation occurs for a duration of 0.5-8 hours.

7. The method of claim 6, wherein the contacting the host cell culture with the second manipulation occurs for a duration of 2 hours.

8. The method of claim 3, wherein the first manipulation of DO is at a set point of 0% DO.

9. The method of claim 3, wherein the second manipulation of DO is at a set point of 100% DO.

10. The method of claim 1, wherein the protein is an antibody.

11. The method of claim 10, further comprising combining the antibody with a drug-linker compound under conditions sufficient to form an antibody-drug conjugate.

12. The method of claim 10, wherein the antibody has at least two engineered cysteine residues.

13. The method of claim 12, wherein the engineered cysteine residues are present in the heavy constant region of the antibody molecule.

14. The method of claim 12, wherein the engineered cysteine residues are present in the heavy chain or light chain variable region of the antibody molecule.

15. The method of claim 1, whereby the protein molecule is re-capped with a cysteine molecule.

16. The method of claim 1, wherein the cysteine cap is an engineered cysteine cap (EC-cap).

17. The method of claim 1, wherein the host cell culture is contacted with cystine on day 10 of the host cell culture.

18. The method of claim 1, wherein the host cell culture is contacted with cystine daily throughout the host cell culture duration.

19. The method of claim 1, wherein the host cell culture is contacted with cystine on the final day of the host cell culture duration.

20. The method of claim 1, wherein the cystine is added at a concentration of between 0.1 mM and 5 M.

21. The method of claim 1, wherein the cystine is added at a concentration of 4 mM.

22. A method for removing and re-forming a cysteine cap from a protein molecule, the method comprising:
    culturing a host cell comprising a protein molecule having at least one capped cysteine residue; and
    contacting the host cell culture with cystine;

simultaneously or subsequent to contacting the host cell culture with cystine, contacting the host cell culture with a first manipulation of DO at a set point of 0%-50%;

subsequent to contacting the host cell culture with DO at a set point of 0%-50%, contacting the host cell culture with a second manipulation of DO at a set point of 20%-100%;

whereby the cysteine cap is removed from the protein molecule and the protein molecule is re-capped with a cysteine molecule.

23. A method for removing a cysteine cap from a protein molecule, the method comprising:

culturing a host cell comprising a protein molecule having at least one capped cysteine residue; and contacting the host cell culture with a symmetrical disulfide;

whereby the cysteine cap is removed from the protein molecule.

* * * * *